(12) United States Patent
Lendenmann et al.

(10) Patent No.: US 10,173,352 B2
(45) Date of Patent: Jan. 8, 2019

(54) METHOD FOR THE PRODUCTION OF STRUCTURED CELLULOSE PATCHES OR ELEMENTS AND DEVICES MADE USING SUCH A METHOD

(71) Applicant: ETH ZÜRICH, Zürich (CH)

(72) Inventors: Tobias Lendenmann, Zürich (CH); Maximilian Fischer, München (DE); Simone Bottan, Zürich (CH); Aldo Ferrari, Zürich (CH); Dimos Poulikakos, Zollikon (CH); Bernhard Winkler, Bern (CH); Martin Grapow, Basel (CH)

(73) Assignee: ETH ZURICH, Zurich (CH)

( * ) Notice: Subject to any disclaimer, the term of this patent is extended or adjusted under 35 U.S.C. 154(b) by 157 days.

(21) Appl. No.: 15/023,215

(22) PCT Filed: Sep. 18, 2014

(86) PCT No.: PCT/EP2014/069882
§ 371 (c)(1),
(2) Date: Mar. 18, 2016

(87) PCT Pub. No.: WO2015/040106
PCT Pub. Date: Mar. 26, 2015

(65) Prior Publication Data
US 2016/0221228 A1 Aug. 4, 2016

(30) Foreign Application Priority Data
Sep. 19, 2013 (EP) .................................... 13185146

(51) Int. Cl.
*A61F 13/00* (2006.01)
*B29C 41/00* (2006.01)
(Continued)

(52) U.S. Cl.
CPC ...... *B29C 41/003* (2013.01); *A61F 13/00021* (2013.01); *A61F 13/00987* (2013.01);
(Continued)

(58) Field of Classification Search
CPC ............. B29C 41/003; A61F 13/00995; A61F 13/00987; A61F 13/00991; C08L 1/00;
(Continued)

(56) References Cited

U.S. PATENT DOCUMENTS

2002/0107223 A1 8/2002 Oster et al.
2010/0121431 A1\* 5/2010 Bertholdt .................. A61F 2/06
623/1.24

FOREIGN PATENT DOCUMENTS

WO 89/012107 A1 12/1989
WO 2008/040729 A2 4/2008
WO 2013/091790 A1 6/2013

OTHER PUBLICATIONS

International Search Report for PCT/EP2014/069882 dated Nov. 28, 2014 [PCT/ISA/210].
(Continued)

*Primary Examiner* — Donald J Loney
(74) *Attorney, Agent, or Firm* — Sughrue Mion, PLLC

(57) ABSTRACT

A method for the self-assembled production of a topographically surface structured cellulose element. First, a mold is provided having on one side a first surface which is in a complementary manner topographically structured and which is permeable to oxygen. Next, a liquid growth medium containing cellulose producing bacteria is provided. Then, the mold is placed to form a interface such that the side of the mold with the first surface is in direct contact with the liquid growth medium, and an opposite side is facing air or a specifically provided oxygen containing gas surrounding. This allows bacteria to be produced and deposit cellu-
(Continued)

lose on the first surface and developing on the interface a surface structured surface complementary thereto, until a cellulose layer with a thickness of the element of at least 0.3 mm is formed. Finally; the element is removed from the mold.

25 Claims, 9 Drawing Sheets

(51) Int. Cl.
    *A61F 13/02* (2006.01)
    *A61N 1/362* (2006.01)
    *C08L 1/00* (2006.01)
    *C08B 1/00* (2006.01)
    *C08L 1/02* (2006.01)
    *B29K 1/00* (2006.01)

(52) U.S. Cl.
    CPC ...... *A61F 13/00995* (2013.01); *A61F 13/023* (2013.01); *A61N 1/362* (2013.01); *A61F 13/00991* (2013.01); *A61F 2013/00157* (2013.01); *A61F 2013/00327* (2013.01); *A61F 2013/00927* (2013.01); *B29K 2001/00* (2013.01); *B29K 2883/00* (2013.01); *C08B 1/00* (2013.01); *C08L 1/00* (2013.01); *C08L 1/02* (2013.01)

(58) Field of Classification Search
    CPC ........ C08L 1/12; C08B 1/00; Y10S 435/8215; Y10S 435/822
    See application file for complete search history.

(56) References Cited

OTHER PUBLICATIONS

Written Opinion for PCT/EP2014/069882 dated Nov. 28, 2014 {PCT/ISA/237].

* cited by examiner

A

B

A 1-20 cm

B

C

METHOD FOR THE PRODUCTION OF STRUCTURED CELLULOSE PATCHES OR ELEMENTS AND DEVICES MADE USING SUCH A METHOD

CROSS REFERENCE TO RELATED APPLICATIONS

This application is a National Stage of International Application No. PCT/EP2014/069882 filed Sep. 18, 2014, claiming priority based on European Patent Application No. 13185146.1 filed Sep. 19, 2013, the contents of all of which are incorporated herein by reference in their entirety.

TECHNICAL FIELD

The present invention relates to the field of production of topographically surface structured cellulose patches or elements and devices such as patches or elements, generally speaking devices, also 3D devices, made using such a method or using elements made using such a method.

PRIOR ART

Wound dressings are designed to support the wounded region, protect it from infection, and, in certain cases, actively promote wound healing by creating a favorable environment for cell growth.

The response to wounding, defined as a breakage of bodily tissue, involves an inflammation phase, a migratory phase and a remodeling phase. The inflammation phase is the acute response to a wound and its purpose is to quickly seal the wound and produce chemical factors that employ cells to migrate into the wound and start the wound healing process. During the migratory phase, cells rapidly migrate into the wound and start laying down provisional extracellular matrix that will be the base of the healed tissue. During the remodeling stage, the newly created tissue slowly matures into its permanent form.

Standard wound dressings facilitate wound healing by: 1. mechanically holding the wound edges together to allow easier cell migration; 2. mechanically sealing the wound to prevent contamination by pathogens; 3. in some advanced dressings providing an environment that actively promotes faster wound healing, usually by exposing the wounded tissue to a hydrated gel. Improved materials for these applications would be desirable.

In plastic surgery commercial silicone implants (e.g. breasts, calf, buttock, chest, biceps) often fail due to foreign body reaction and scar-tissue encapsulation. Also for such applications improved materials/coatings would be desirable.

In cosmetics disposable flat and unstructured cellulose masks are currently sold (e.g. face, hands and feet) as masks that enhance skin hydration, as well as the absorption of metabolic waste products and the release of nutrients or other compounds to the skins.

SUMMARY OF THE INVENTION

It is therefore an object of the present invention to propose new methods for the manufacturing of materials for these applications, in particular topographically surface structured patches or coating, most particularly cellulose patches or elements and devices such as patches or elements, generally speaking including devices, also 3D devices, made using such a method or using elements made using such a method.

One important element of the proposed invention is the description of a simple and cost-effective procedure to transfer micro or nano-structured topographical features on the surface of bacterial cellulose. The process can be performed with minimal costs and laboratory equipment and does not require trained personnel. The process can be fully automated and exploits the self-assembly of cellulose by bacterial strains such as (but not only) *Acetobacter Xylinum* or *Gluconabacter Xylinum*. The protocol is schematized in FIG. 1.

The process of Self Assembled Biolithography (SAB) is based on a simple technique which takes inspiration from soft lithography (SL). However, while for SL the molding of the target elastomer requires trained personnel and several passages, thus resulting in a time consuming and delicate procedure, the SAB is fully based on the natural process of cellulose production by bacteria. SAB interferes with this process locally directing the assembly and polymerization of cellulose fibers, and thus resulting in a high-fidelity negative replica of the surface geometry presented by the mold.

The natural porosity of bacterial cellulose can be controlled modulating the growth conditions of bacterial (Oxygen (partial) pressure, glucose concentration, bacterial strain) or can be modified on already assembled cellulose meshes with post-production chemical treatments. However, to our knowledge, the transfer of regular topographic arrays on the surface of contiguous cellulose matrixes of sufficient thickness to lead to a product that can be handled and commercially used has never been achieved.

The number of applications of bacterial cellulose is countless, and several items made of bacterial cellulose are currently available on the market for cosmetic or medical applications. Additionally, bacterial cellulose has been proven to have superior mechanical properties and to be virtually inert upon implantation in animals. FDA approval of this material for implantable biomedical devices will further increase the number of medical applications profiting from bacterial cellulose. The proposed invention adds a totally independent, critical, physical parameter to control the interaction between human tissues and bacterial cellulose. Controlling the surface topography of the cellulose, the adhesion, proliferation, differentiation, migration and apoptosis of cells can be modulated or directly induced. Therefore, the cost-effective engineering of the material surface may provide a full range of novel properties that improve the biocompatibility and effectiveness of biomedical devices featuring bacterial cellulose.

So a Self-Assembled Biolithography (SAB) is proposed as a new protocol to introduce pre-defined geometries in the micron and submicron scale on the surface of bacterial cellulose. The protocol applies the principles of elastomer-based soft lithography and allows for a cost-effective replica molding upon the generation of a cellulose network. In particular, a mold of an oxygen permeable material, preferably an oxygen permeable polymeric material, and most preferably a siloxane, e.g. (polydimethylsiloxane) PDMS mold is created via standard soft-lithography on a molding mask. The molding mask featuring the target geometry can be made of any thermoplastic polymer and is generally (but not exclusively) obtained via standard hot embossing. The PDMS mold is then placed at the interface with the bacteria growth media and represents a gas-permeable scaffold fostering the polymerization of bacterial cellulose. SAB yields a patch of cellulose featuring a negative replica of the surface geometry presented on the PDMS mold, and therefore equal to the initial molding mask. The surface-structured bacterial cellulose patch can be finally peeled from the PDMS mold without further passages. Both the PDMS mold and the original molding mask can be used for several cycles without deterioration. The SAB procedure allows a high-fidelity transfer of any texture in the micron and submicron range from a PDMS mold to bacterial cellulose and does not require any further action by the operator. In all, we invented a new method to couple the bio-chemical properties of bacterial cellulose to the control of cell-material interaction with interface textures. We envision the exploitation of this new technology to produce improved biological coatings, wound dressings, and/or cosmetics with enhanced interaction with human tissues.

The invention more specifically proposes a Self-Assembled Biolithography (SAB) protocol including the following steps: A mold, preferably a PDMS mold, is created, preferably via standard soft-lithography casting PDMS on a plastic mask (upper row). The mask featuring surface topography can be made of a thermoplastic polymer and is generally (but not exclusively) obtained via standard hot embossing. SAB using the mold as a structuring template using a cellulose producing strand in a growth medium on the topographically structured surface and allowing for oxygen to pass through the mold produces a flat cellulose patch with a negative replica of the surface geometry presented by the (PDMS) mold. The mold is simply placed at interface with the growth media and represents a gas-permeable scaffold inducing the polymerization of bacterial cellulose. The cellulose patch can be finally peeled from the PDMS mold without further passages.

As such there have been several attempts to surface texture cellulose structures. It has for example been proposed to use existing cellulose material and to emboss a surface structure mechanically. However using this technique leads to significant density changes in the resulting cellulose material, leads to destruction of the cellulose structure on a molecular level, resulting in insufficient homogeneity. In addition to that, in this case there is only the surface structure, while in the proposed approach there is not only the surface structure but also, due to the self assembled growth, a particular orientation of the cellulose fibres in this surface structure which is associated with and related to the surface structure. This has additional effects which cannot be achieved by embossing techniques.

Other approaches have tried to self assemble cellulose on a structure, however in all these cases no contiguous layers could be produced but only gridlike structures and in addition to that, due to the fact that they were grown on templates without allowing oxygen to be present on the interface between the template and the place where cellulose is generated, the resulting cellulose structures are inherently extremely thin and cannot be handled. So all these approaches did not lead to products which can actually be commercially used.

More generally speaking, the present invention relates to a method for the self assembled production of a topographically surface structured cellulose element. The method involves a first step with the following elements:

a mold with on one side a first surface which is in a complementary manner topographically surface structured and which is permeable to oxygen is provided, a liquid growth medium containing cellulose producing bacteria is provided, the mold is placed to form a liquid/air interface of the liquid growth medium such that the side of the mold with the first surface is in direct contact with the liquid growth medium, and with an opposite side is facing air or a specifically provided oxygen containing gas surrounding, allowing for said bacteria to produce and deposit cellulose on said first surface (4) and developing on the interface therewith a topographically surface structured surface complementary thereto, until a contiguous cellulose layer with a thickness of the element (10) of at least 0.3 mm, preferably of at least 0.4 mm, most preferably of at least 0.5 mm or at least 0.75 mm, is formed.

In a subsequent second step the element is removed from said mold.

The term "topographically surface structured" according to the invention is in particular to be understood as follows:

The surface is provided with a topography, i.e. a 3D surface profile, which is a regular array of geometric features in at least one direction of the surface plane. This regular array of geometric features is preferably defined by the following parameters:

Individual feature size (vertical and lateral) which can span between a few tens of nm (10 nm or 20 nm) to tens of microns (10 to 20 mum).

Feature periodicity (inter-feature distance): Topographic features can be spaced isotropically (the inter-feature distance is equal in all directions in the plane) or anisotropically (the inter-feature distance is lower or bigger in at least one direction than in another direction in the plane)

Feature orientation—Anisotropic features (for example rods) may be preferentially oriented in one direction, e.g. all perpendicular to the main surface or all aligned along one common directional vector which is not perpendicular to the plane but still tilted with respect to the plane, i.e. not in plane, or randomly oriented.

Order/disorder: When producing an array of topographic features (for example pillars as given above and further detailed below) the position of the features in the crystal array can be defined with a certain tolerance from the ideal xy position (corresponding to a perfect crystal structure). Increasing the tolerance (for example as % deviation from ideal crystal structure) it is possible to introduce a controlled amount of disorder. This order/disorder ratio can have a great impact on the cell response.

This notion of "topographically surface structured" is thus different from a normal surface roughness (what is obtained by simply growing cellulose), which is a random and not regular structure, and which roughness is characterized as the deviation of a surface from a perfectly flat profile. In this definition of "topographically surface structured" two surfaces can have similar roughness but display different topographic features, or feature arrangement.

The main practical difference between a topographically engineered cellulose surface and a native rough cellulose is that in the first case essentially ALL cells interacting with the surface will receive the same rationally-designed topographical signal, in the second case each cell (depending on the specific region of interaction) will receive a different set of signals. For this reason a coordinated cell response (such as the one required for wound healing or for the inhibition of inflammatory reaction) can ONLY be obtained using a topographically engineered surface.

One of the key and unexpected properties of the resultant structures is the finding, that they are stable upon dehydration/rehydration so there is a shape memory, the shape is preserved if an element is dried (and the topographically structured surface collapses) and subsequently wetted again (which leads to a swelling and a regeneration of the topographically structured surface). This simplifies and extends storage and makes the structures less prone to degradation.

As medical device, surface structured cellulose can be used for obtaining the following effects, alone or in combination:

Improve efficiency and speed up closure time in wounds
Guide, align, orient cells
Promote migration
Demote or promote cell adhesion
Prevent or stimulate cell activation
Minimize inflammatory response
Minimize fibrotic tissue deposition
Minimize foreign body reaction
Reduce Scar formation
Improve mechanical properties of regenerated tissue According to a first preferred embodiment, the element has a thickness in the range of 0.5-10 mm or even up to 15 mm.

Preferably, the mold has a diffusivity to oxygen of at least $10^{-6}$ cm$^2$/s.

Preferentially, the mold, which can be a two-dimensional or three-dimensional mold, is made of siloxane, preferably PDMS, preferably produced in that a topographically complementary structured mask element is used as a template for a liquid applied or injected substrate material, preferably in a soft lithography process, optionally followed by a cross-linking and/or polymerization step, further optionally followed by a surface treatment step, preferably a plasma treatment step on the topographical surface.

The first surface can, according to yet another preferred embodiment, have a topographical structure in the form of a two-dimensional array of pillars, indentations, in the form of an array of ridges/grooves or in the form of a two-dimensional crossing structure or honeycomb patterned structure. So also the negative of a regular pillar structure, a two-dimensional array of indentations, is possible.

Generally speaking, the width of the positive structures, in particular of the ridges and/or of the negative structures, in particular of the grooves, is in the range of 0.5-100 μm, wherein preferably the width of the ridges is in the range of 0.5-5 μm and the width of the grooves is in the range of 0.5-5 μm, preferably both widths being essentially equal.

Even more preferably, the ridges have a height h of at least 0.4 μm, preferably in the range of 0.5-5 μm or in the range of 0.5-2 μm, more preferably in the range of 1-2 μm.

Generally speaking, preferably the (essentially all identical) pillars preferably all and regularly have a round, oval or polygonal cross section, preferably a regular polygonal, most preferably triangular, square, pentagonal or hexagonal cross-section.

The two-dimensional array of pillars can have a periodicity in one dimension in the surface plane, preferably in two or three different directions in the surface plane in the range of 5-50 μm, preferably in the range of 7-15 μm. Preferred is in case of e.g. hexagonal pillars an arrangement where there are three such periodicity directions skewed at 0°, 60° and at 120°. Preferably the periodicity is the same along the different directions in the surface plane.

The individual pillars can have a lateral extension in the range of 2-20 μm, preferably in the range of 4-10 μm.

Further preferably the individual pillars can have a height in the range of 0.2-5 μm, preferably in the range of 0.5-2 μm.

Preferred are regular two-dimensional arrays of hexagonal pillars, where preferably the periodicity is twice the lateral extension of the individual pillars.

When talking about pillars as detailed above in terms of dimensions this preferably also includes corresponding negative structures, so structures where there are no regular pillars but regular indentations having the shape of these pillars.

In the second step the mold with the element on its topographically surface structured first surface can be immersed into a liquid, and the element can be removed, preferably peeled off, from said first surface in said liquid, wherein said liquid preferably can be a NaOH solution, preferably with a concentration in the range of 0.5-2M, preferably around 0.5M. According to yet another preferred embodiment, after the second step the element is heat-treated, preferably by keeping it at a temperature above room temperature in a liquid, preferably in a NaOH solution, for a time span of more than 10 minutes, preferably of more than 60 minutes, most preferably at a temperature above 60° C.

The invention furthermore relates to a topographically surface structured cellulose element being in the form of a contiguous layer with a thickness in the range of 0.5-5 mm, preferably produced or producible using a method as outlined above, and having a topographical surface structure with a height in the range of 0.5-2 μm (micrometer), and in case of a groove/ridge topographical structure α periodicity of the structure in the range of 0.5-100 μm (micrometer).

This topographically surface structured cellulose element can, in particular for healing patch applications, be a patch, and this patch is generally bi-dimensional, so it extends as a flat layer in two dimensions and each dimension is larger than 1 mm, preferably larger than 2 mm, and it can be as large as 5-20 cm. The 2D shape of such a patch can be depending on the needs, e.g. square, circle, triangle et (see also FIG. 9). Shape and Topography can be optimized depending on the type of application. E.g. parallel gratings can be used, in case of healing patch applications, for longitudinal wounds, confocal gratings for burn or circular wounds. So in other words topographical surface structure can be an array of parallel arranged ridges/grooves (normally parallel to one edge of the patch), concentrically converging ridges/grooves (for example in case of a circular patch or in case of an oval patch), and/or adaptively bent and locally parallel arranged ridges/grooves (see FIG. 9c for example).

Furthermore the invention relates to the use of such an element as a patch for wound healing and/or cosmetic applications, as a coating for an implant or plastic surgery structure.

Possible is also the use of such a patch, made e.g. as a 3D element, e.g. in the form of a pouch, for covering an implant or for forming an implant as such.

In this sense the present invention also relates to a topographically surface structured element, wherein it has the form of a three-dimensional structure, with or without support element, and wherein preferably it has the form of a cover, bag, coating, pouch or pocket into which an implantable object can be put or to cover an implantable object, wherein preferably the implantable object is selected from the following group: cardiovascular device, in particular a pacemaker; cosmetic implant, preferably in the form of a breast implant, cuff implant, pectoral implant, biceps implant, buttock implant, gluteal implant; orthopedic prosthesis; a sensor and/or electrical stimulation device; draining system, preferably a catheter; pump or tubing system; ophthalmological device; hearing device; bionic device.

The following uses of such 3D coatings/pouches/covers/pockets/bags are thus generally possible:

Pacemakers

Breast implants other cosmetic implants (e.g. cuff, pectoral, biceps, buttock/gluteal, etc.)

other implantable medical devices e.g.

orthopedic prosthesis cardiovascular devices sensors and electrical stimulation devices draining systems such as catheters for urinary incontinence, ventriculo-peritoneal shunts, etc.

pumps and tubing systems, such as controlled drug infusing systems for chronic pain therapies, etc.

ophthalmologic devices earing devices bionic devices such as robotics

Generally speaking as concerns possible fields of application, the following can be said:

1) Plastic Surgery:

commercial silicone implants (e.g. breasts, calf, buttock, chest, biceps) fails due to foreign body reaction and scar-tissue encapsulation. Cellulose prevents both these reactions. Enveloping of these implants in micro-patterned cellulose not only prevents negative reactions by the human body, but also improves a positive cellular reaction in the surrounding tissues. Micro-patterned cellulose would add market value to existing implants, by drastically reducing their failure rate.

2) Cosmetics:

disposable cellulose masks are currently sold (e.g. face, hands and feet) in cosmetics as masks that enhance skin hydration, as well as the absorption of metabolic waste products and the release of nutrients or other compounds to the skins. Commercial cellulose masks do not feature any surface topography. Micro-patterned topography would enhance i) mass transport with the skin by increasing the surface in contact with water or other liquids, ii) cellular response by apical guidance on the epithelial tissue. SAB can be adopted to develop micro-patterned cellulose cosmetic masks: SAB would increase performances of cosmetic masks and ultimately add market value to them.

3) Patch and Wound Healing:

cellulose is a fully biocompatible material that is ideal for contact with damaged tissues (artificial skin for burn treatments, occlusive dressing for chronic wounds such as diabetic ulcers, common friction wounds, etc. . . . ). Micro-patterned topography stimulates cellular response, in particular of human dermal fibroblasts (HDF), in terms of spreading, proliferation, differentiation and directional migration, which ultimately enhance the efficiency of wound healing. SAB can be used to fabricate micro-patterned cellulose patches for the handling of wounds.

Further preferred embodiments of the invention are outlined in the appended claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 8:
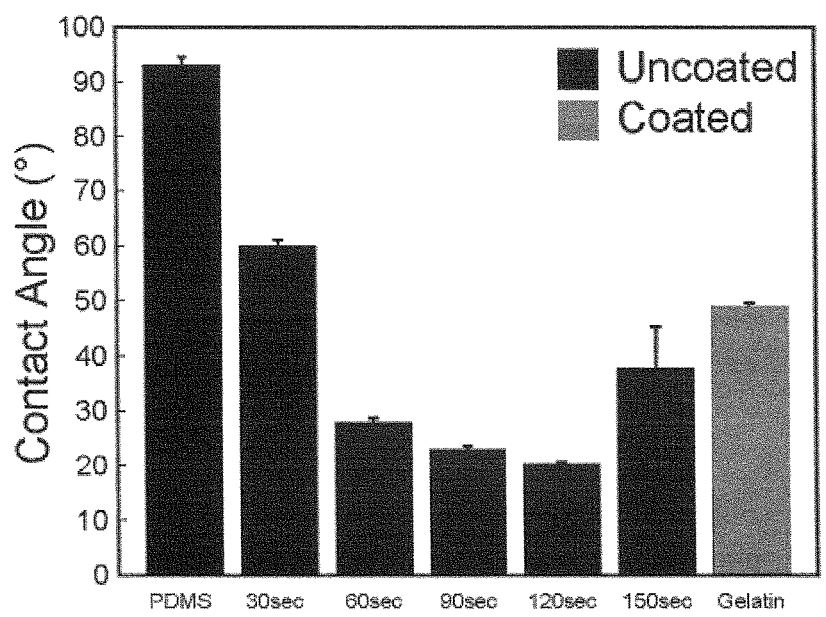
FIG. 8 shows the water static contact angle measured on the active PDMS mold surface upon different plasma treatments, the contact angle of untreated PDMS molds is compared with the contact angle of patches treated with low power (10 W) plasma for 30, 60, 90, 120, and 150 seconds and with the contact angle of gelatin coated PDMS.

PDMS Mold Fabrication:

PDMS molds were made of Polydimethylsiloxane (PDMS, Dow Corning, USA) at 1:10 mixing ratio. The mixed PDMS was degassed in a vacuum chamber for 10 minutes to remove trapped air and poured at 500 µm thickness onto a micropatterned cyclic olefin copolymer (COC) mask consisting of parallel grooves with 2 µm period, 1 µm groove width and 0.6 µm groove depth. Subsequently, the PDMS was briefly degassed for a second time and cured for 4 hours at 60° C. The cured PDMS molds were separated from the mold with tweezers and cut into squares of 1 cm² with a scalpel. Blank molds were similarly created by pouring PDMS onto flat COC substrates for comparison purposes. Subsequently, all patches were left in ethanol overnight to dissolve any uncrosslinked material. The molds were then treated with oxygen plasma to increase the hydrophilicity of the surface. A process time of 120 seconds at 10 W was chosen after testing a range of intervals from 30 to 150 seconds as the one yielding the lowest contact angle (20.2±0.5°). FIG. 8 shows the testing so the water static contact angle measured on the active PDMS patch surface upon different plasma treatments, the contact angle of untreated PDMS patches is compared with the contact angle of patches treated with low power (10 W) plasma for 30, 60, 90, 120, and 150 seconds and with the contact angle of gelatin coated PDMS. The stiffness of the resulting patches was measured by uniaxial testing and their Young's modulus was calculated to be 1.53±0.057 MPa.

Figure 1:
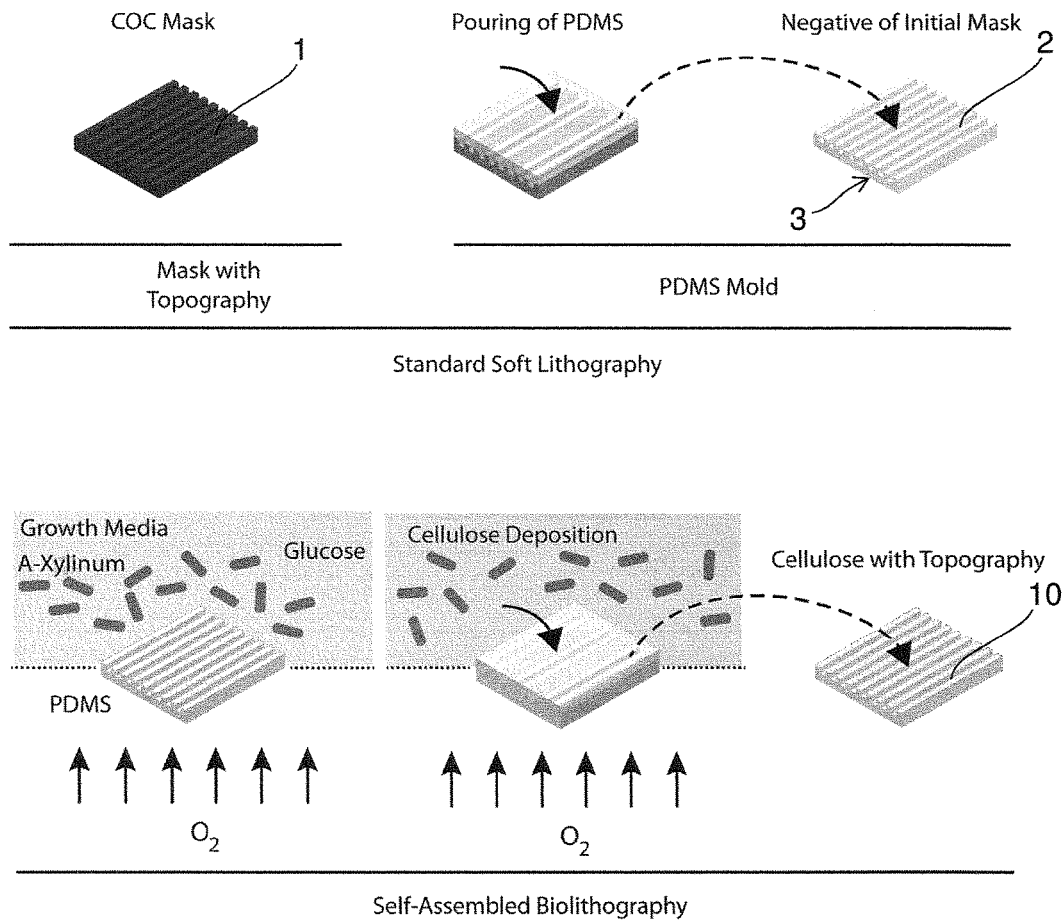
FIG. 1 shows a schematic representation of the Self-Assembled Biolithography (SAB) protocol; a PDMS mold is created via standard soft-lithography casting PDMS on a plastic mask (upper row); the mask featuring surface topography can be made of any thermoplastic polymer and is generally (but not exclusively) obtained via standard hot embossing; SAB (lower row) produces a flat patch with a negative replica of the surface geometry presented by the PDMS mold; the mold is simply placed at interface with the growth media and represents a gas-permeable scaffold inducing the polymerization of bacterial cellulose; the cellulose patch can be finally peeled from the PDMS mold without further passages.
Figure 2:
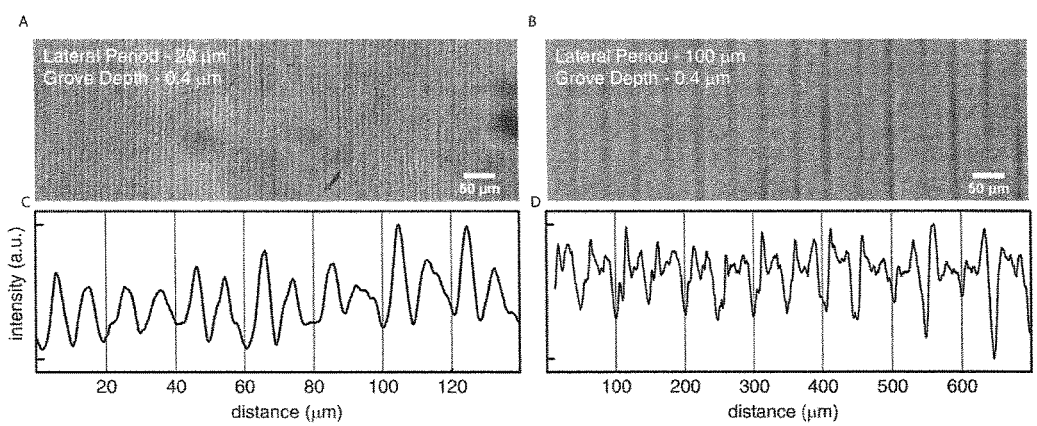
FIG. 2 shows the surface topography on bacterially produced cellulose; gratings generated on cellulose patches by means of SAB; transmission images of gratings with grove depth of 0.4 µm, lateral period of 20 A), or 100 B) µm; respectively; C) and D) Intensity profiles of the images reported in panels A and B.
Figure 3:
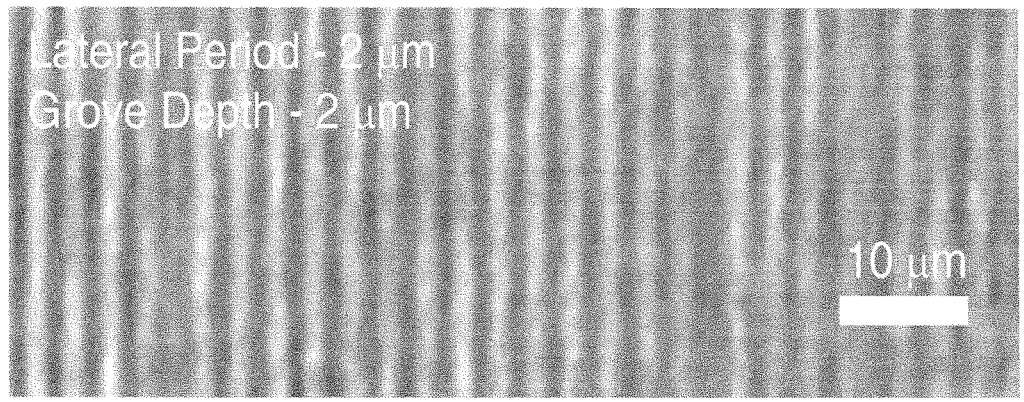
FIG. 3 shows gratings with high aspect ratio generated on bacterial cellulose by means of SAB.
Figure 4:
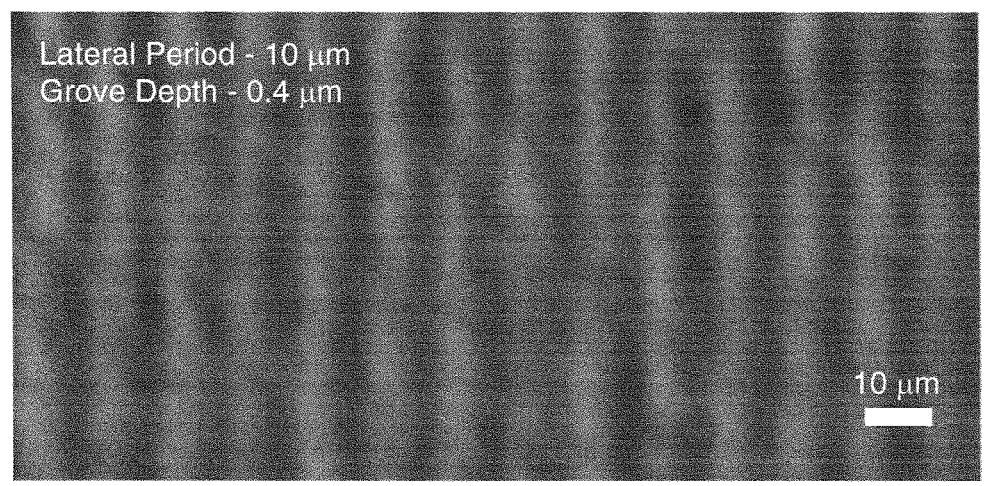
FIG. 4 shows the control of vertical feature size in SAB; transmission images of gratings with lateral period of 10 µm and grove depth of 0.4 A) or 1 µm B); respectively.
Figure 4:
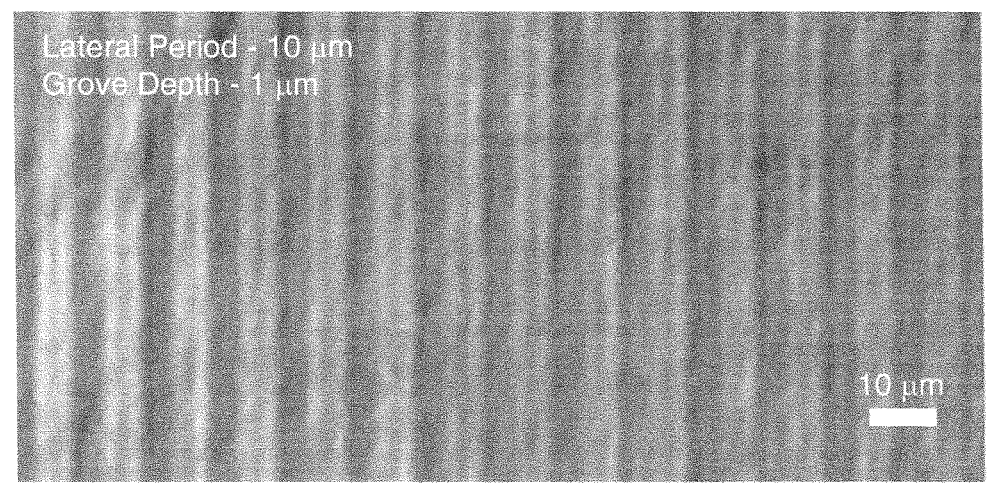
Figure 5:
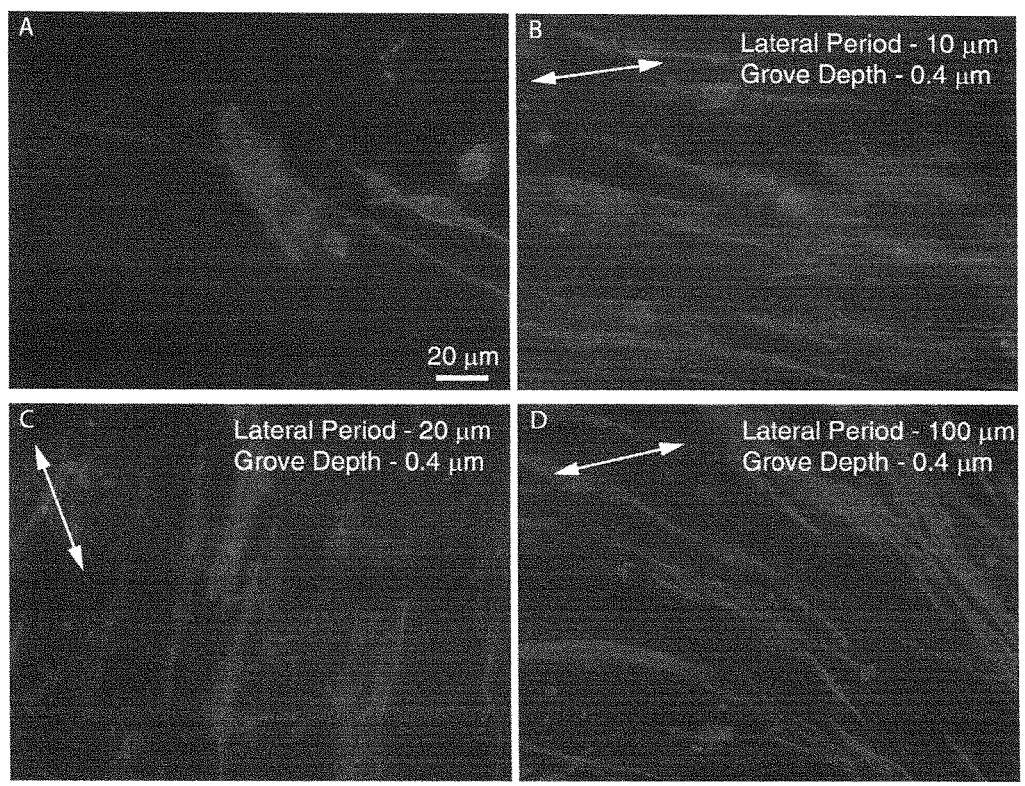
FIG. 5 shows the growth of human dermal fibroblast (HDF) on gelatin-coated bacterial cellulose; immunostaining of HDF revealing the cell nuclei and the actin cytoskeleton; few non polarized cells adhere and grow on flat patches A) while denser cell layer can be obtained on SAB textured cellulose; here, HDF elongate along the direction of the topography and in particular on gratings with lateral period of 10 B) or 20 µm C); reduced alignment is obtained on gratings with lateral period of 100 µm D); the direction of the gratings is indicated by the white arrows.
Figure 6:
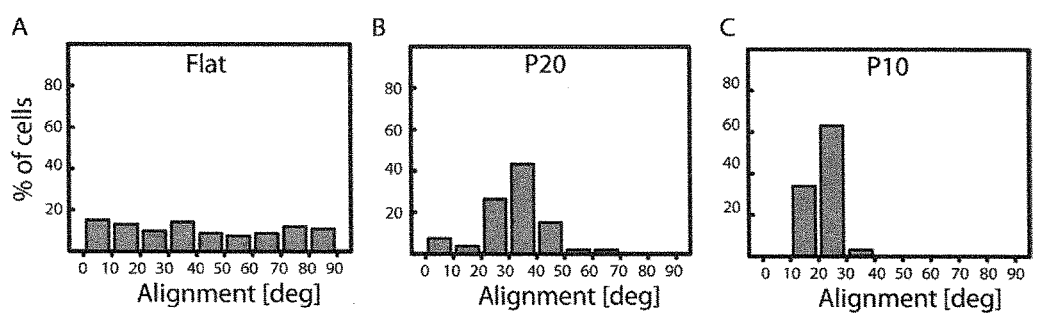
FIG. 6 shows the distribution of human dermal fibroblasts (HDF) alignment on the cellulose patches: angular orientation with respect to the direction of the gratings; flat sample with no surface topography A), and gratings generated on cellulose patches by means of SAB: grove depth of 0.4 µm, lateral period of 20 B), or 10 C) µm, respectively; the cells show a random distribution on the flat patch (A); their orientation becomes more uniform when the cellulose patches feature surface topography with micro-gratings (B and C)

The mold 2 has grooves 6 with a width f and ridges 5 with a width e. This shall be illustrated in somewhat more detail in the context of FIG. 7, specifically FIG. 7a, in which a cut essentially perpendicular to the running direction of the pattern on the mold 2 is shown. In this case the pattern is a regular rectangular pattern, where both widths e and f are equal, and where the pattern angle α is 90°. The length l of the actual pattern should have a minimum length, namely the pattern period p should be smaller than 10 µm [micrometer] and the pattern length l should be larger than 1 mm. Normally this length l is equal to the full with d of the mold 2 as illustrated in FIG. 1. The ridges have a height h (or the grooves have a depth), which can be within the boundaries as outlined above.

The shape of the pattern does not need to be a regular rectangular shape as illustrated in FIG. 7a. The ridges can also be of at least partly trapezoidal shape as illustrated in FIG. 7b, they can be of triangular shape as illustrated in FIG. 7c (it is also possible that the triangles meet at the bottom of the ridges leading to a zigzag shape), and they can also be rectangular with rounded edges as illustrated in FIG. 7d (the rounded edges can be at the top corners of the ridges as illustrated in FIG. 7d, they may however also be or alternatively be at the bottom edges of the grooves).

Figure 7:
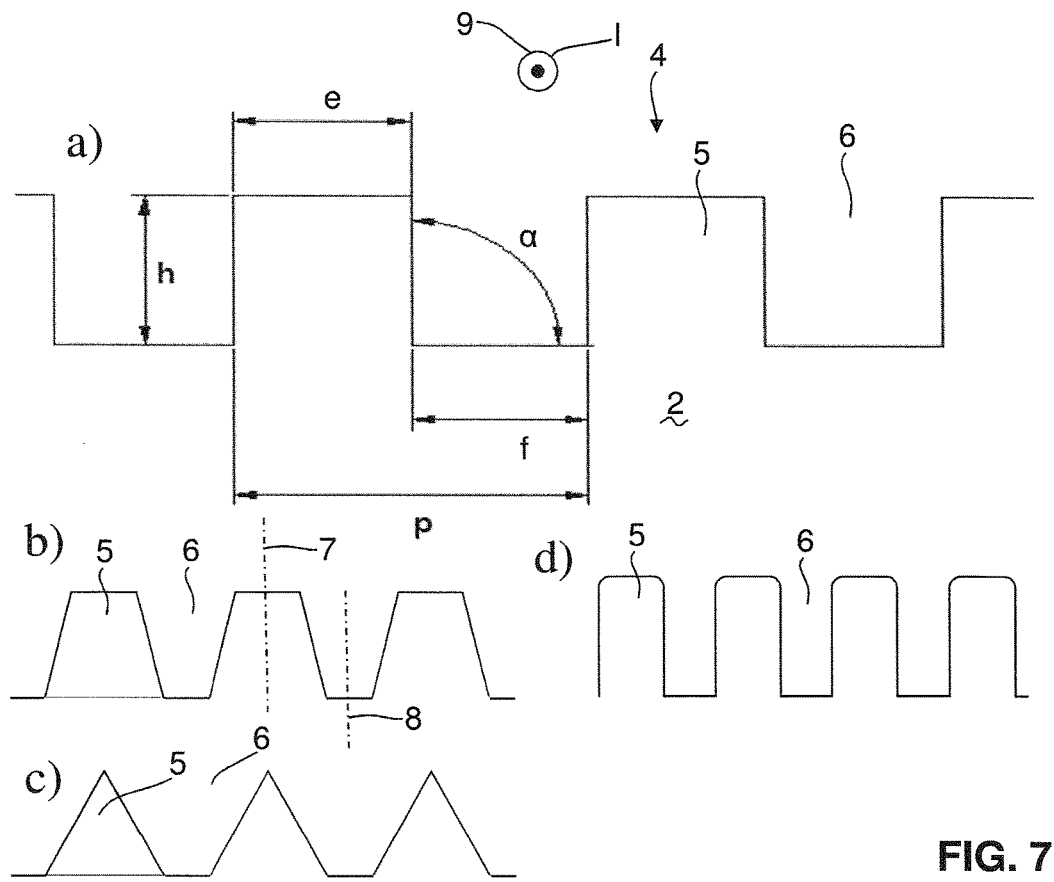
FIG. 7 shows a cut essentially perpendicular to the running direction of the grooves/ridges with the possible dimensions schematically illustrated in a), and in b)-d) possible alternative shapes of the grooves/ridges of the PDMS mold.

Within FIGS. 1 and 7 only situations are shown where the pattern essentially extends along a single linear direction. It is however also possible to have a bent structure along the direction 9, if growth of the cellulose producing cells is to be induced along such a bend. The length l with the limits as outlined above is in this situation to be understood as the length along such a bent shape.

Figure 9:
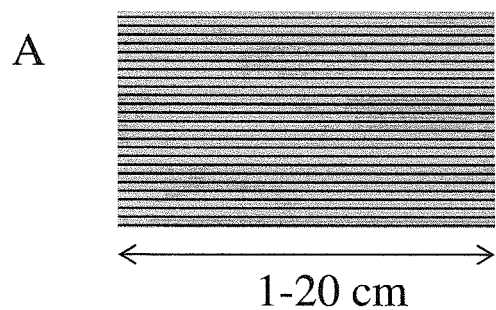
FIG. 9 shows possible geometrical shapes of topographical arrays on healing/dressing patches, wherein in A) the shape for a longitudinal wound is shown, in B) the shape for a circular wound, and in C) the shape for a more complex wound are given.
Figure 9:
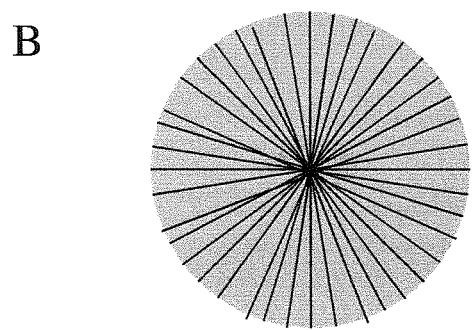
Figure 9:
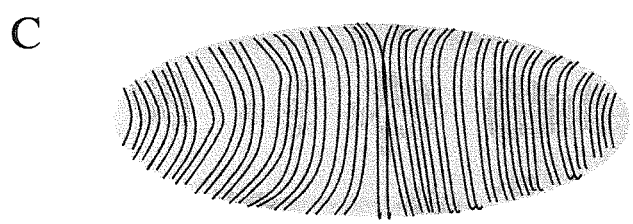

Possible geometrical shapes of topographical arrays on healing/dressing patches are illustrated in FIG. 9. While the basic geometry is gratings, as longitudinal arrays of alternating ridges and groves, this may only be useful and appropriate to longitudinal wounds or burns, provided preferably that the anisotropic topography is aligned perpendicular to the wound when the patch is applied.

However, more complex geometries can be realized to interact with circular or complex-shaped wounds or burns. These geometries refer to the macroscopic pattern while at the micro-scale or submicron scale the topographical features may retain the same or similar feature size and periodicity. Visual examples are given below for the case of a longitudinal wound A), of a circular wound B) or of a complex shaped wound C) in FIG. 9.

Growth of the Cellulose Patch on the Mold:

Materials:

| Name | Concentration |
|---|---|
| Acetobacter Xylum (ATCC - strain 700178)[1] | 1 ml for 20 ml of medium |
| Complete Medium (see below) | 1x |
| PDMS Mold made as described above | |
| Plastic support for culture | |

[1]A. Xylinum belongs to the family of bacteria that ferment carbohydrates to vinegar and is commonly found in soil and decaying fruit. It is peculiar for its cellulose production. Also other bacteria can be used having similar properties.

Procedure:

| Medium composition and preparation | |
|---|---|
| Elements | Amount |
| $KH_2PO_4$ | 7000 mg |
| $(MgSO_4)7H_2O$ | 2130 mg |
| $H_3BO_3$ | 4.3 mg |
| Nicotinamide | 0.7 mg |
| $FeSO_4*7H_2O$ | 9.5 mg |
| $Na_2HPO_4*12H_2O$ | 3380 mg |
| $(NH_4)_2SO_4$ | 3540 mg |
| Ethanol | 4730 mg |
| Distilled Water | 1 liter |

The resulting solution is autoclaved for 30 minutes at 121° C. After cooling down to room temperature, 50 ml of a filtered Glucose solution (50% in distilled water) is added.

Set-Up of the Bioreactor:

For a 10 cm Petri dish.

Take 1 ml of homogenized cellulose (containing bacteria) and mix with 20 ml of medium within a sterile falcon tube (50 ml)

Pour the mixed cellulose and medium into the final dish

Place the PDMS mold on top taking care that no air bubbles are trapped between the liquid medium and the PDMS mold. Bubbles may result in inhomogeneities in the final cellulose patch, so should be avoided.

The PDMS patch will be floating on the medium, therefore it is generally more convenient to use a container that is slightly bigger than the mold.

The bioreactor is carefully placed in the incubator and maintained at 29° C., in a humidified environment (70% humidity)

Let bacteria grow for a sufficient time. The incubation time is proportional to the desired total thickness of the resulting cellulose patch. The following table provides some experimental indication of this correlation:

| Incubation time | Final patch thickness |
|---|---|
| 24 h | 2 mm |
| 48 h | 3 mm |
| 96 h | 4 mm or thicker |

These values can be influenced by increasing the oxygen (partial) pressure across the mold.

Harvesting of the Cellulose Patch:

At the end of the fermentation period the PDMS mold and the cellulose patch are removed from the bioreactor. They will stick together.

The PDMS mold and the cellulose patch are immersed into a NaOH (1M in distilled water) solution at room temperature The cellulose patch is carefully peeled off the PDMS mold within the solution.

The PDMS mold is removed from the solution

The cellulose patch is left in the NaOH solution.

The NaOH solution with the cellulose patch is then kept at 80° C. in an oven for 80 minutes (i.e. the whole patch is immersed in the NaOH solution; prior to that, bacteria and medium are trapped within and at the surrounding of the cellulose; this step removes/washes (or "anneals") the bacteria; the next steps are to replace NaOH with water).

The NaOH solution is then removed and distilled water is added.

The cellulose patch is washed with fresh distilled water 4 times for 1 h each to remove media residues The cellulose patch (which has the character of a hydrogel) is then washed with a 95% ethanol solution and then stored in ethanol until use.

This procedure yields a semi-transparent cellulose patch (in the visible spectrum). To improve transparency (up to 90% of incident light) longer incubation in ethanol (up to 1 week) can be used.

Figure 10:
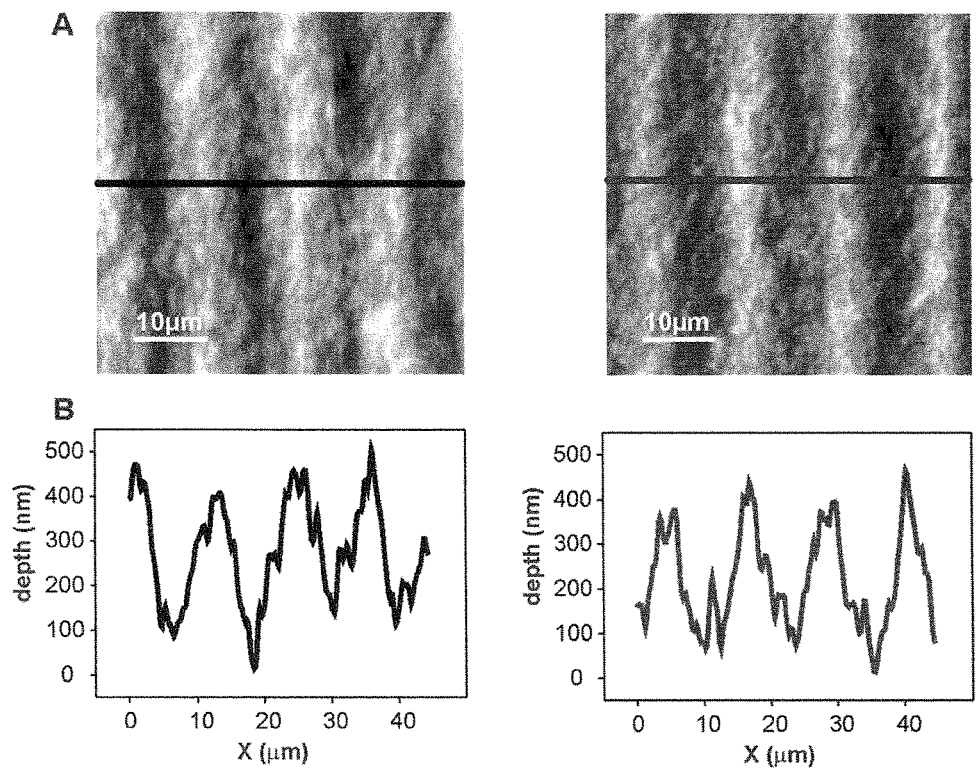
FIG. 10 shows the vertical characterization of structured biocellulose patches before de-hydration (left) and after re-hydration (right); top (A): atomic force micrographs of patches featuring gratings; bottom (B): corresponding height profiles.

FIG. 10 illustrates that the resultant structures are stable upon dehydration/rehydration. The surface topography of the initially produced hydrated patch was measured with the resulting characterization illustrated on the right side. Then the patch was dried out and subsequently the patch was rehydrated again and the surface structure of the same region of the patch was measured, the results being given on the right side. The same depth and periodicity is established after rehydration as before the drying. No deterioration or change in terms of periodicity and/or depth and/or shape of the structures initially established could be observed.

Figure 11:
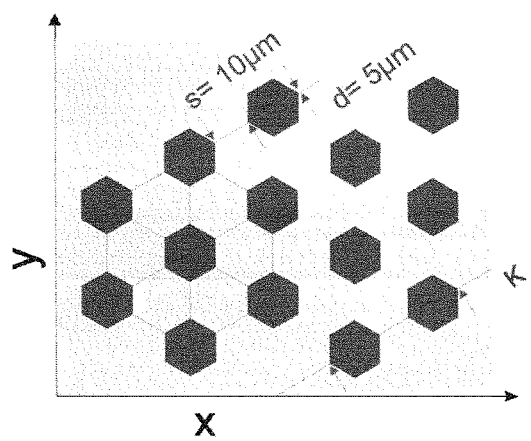
FIG. 11 shows (top) a top view onto a schematic pattern for the topographically surface structured cellulose element wherein the pillars are of hexagonal cross-section (hexagonal pack) and (bottom) a cut perpendicular to the surface plane along line K in the top figure.
Figure 11:
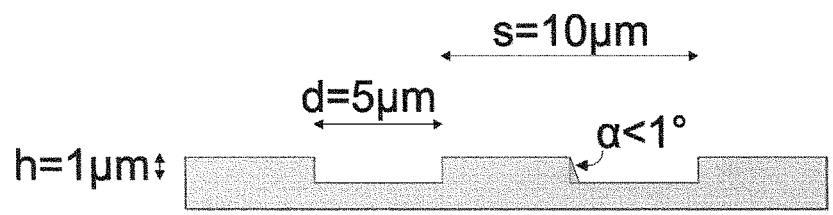
Figure 12:
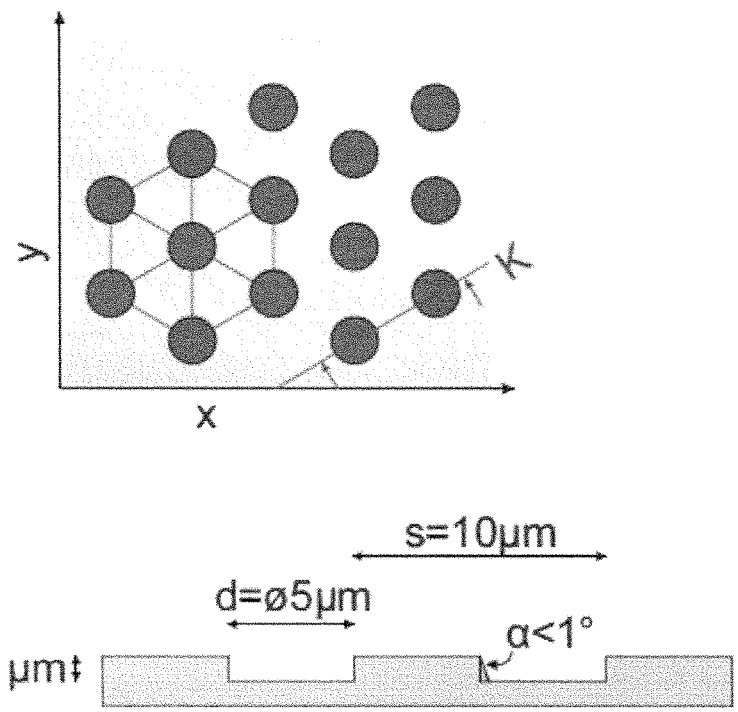
FIG. 12 shows (top) a top view onto a schematic pattern for the topographically surface structured cellulose element wherein the pillars are of round cross section and (bottom) a cut perpendicular to the surface plane along line K in the top figure.

FIGS. 11 and 12 schematically illustrate possible topographies as implemented in the corresponding mould, so the pillars to be generated in the cellulose element are corresponding indentations in the mold surface. In FIG. 11 a hexagonal structure is shown, where a regular array of regular (equal side length, fully symmetric) hexagonal cross-section indentations, finally giving rise to corresponding hexagonal pillars in the cellulose patch, are arranged in a 2D array, in lines along three skewed axes tilted by 60°/120° relative to each other. The maximum inclination angle of the vertical surfaces is preferably, in the mould, smaller than 1°. FIG. 12 illustrates a respective arrangement where the cross section of the indentations is circular, leading to cellulose patches with circular cross-section pillars.

Figure 13:
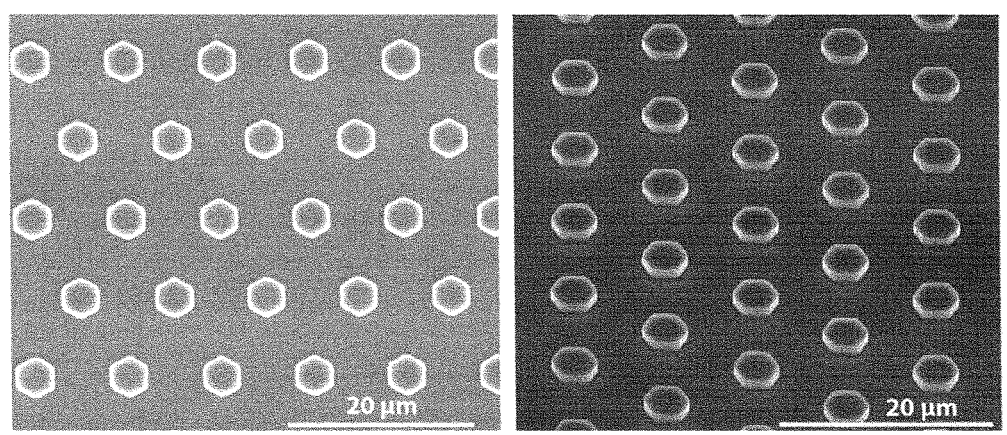
FIG. 13 shows SEM images of hexagonal pack pillar structure on silicon wafer: top view (left) and 45° perspective view (right)

As pointed out above, pillar structures are preferred, but also the corresponding negative structure is possible, i.e. a structure where there is a regular two-dimensional array of indentations, and in which the indentations are all essentially identical. In FIG. 13 a mold structure is shown for making a cellulose patch having a regular array of hexagonal indentations as a surface topography.

In Vitro Vivo Studies of Patches of Mice:

Animal tests were performed on Male C57BL/6J mice with a body weight of 25 to 35 g (n=18) in order to assess:
1. Wound healing performance of cellulose patches with topographically engineered surface.
2. Inflammatory and revascularization process in presence of cellulose To study the revascularization process the modified dorsal skin fold chamber (MDSC) was used. Briefly, for chamber implantation, two symmetrical titanium frames were mounted on a dorsal skin fold of the animal. One skin layer was then completely removed in a circular area of 15 mm in diameter, and the remaining layers (consisting of striated skin muscle, subcutaneous tissue and skin) were covered with a glass cover slip incorporated into one of the titanium frames. Before skin grafting, a recovery period of 3 days was allowed. Then, skin and most parts of the hypodermal fat layer were carefully removed in a circular area of 7 mm in diameter from the back of the chamber in order to create an artificial full-thickness wound. The defect on the back of the chamber was then covered with bacterial cellulose substrates and covered with a glass cover slip incorporated into the other titanium frame. Surface-structured bacterial cellulose substrates were placed with gratings directed towards the wound bed. Additionally, to investigate the biocompatibility of bacterial cellulose substrates, all animals received a replica of the same bacterial cellulose substrate in a skin pocket in the groin.

The overall results have shown minimal inflammation in the wound bed in the presence of bacterial cellulose patch. This was as low as with a full skin graft of the same animal (used as control).

Therefore bacterial cellulose is confirmed as an ideal material for wound treatment and implantation. Additionally, insights from quantitative histological collagen formation analysis and distribution revealed that the group treated with topographically engineered cellulose had (after 21 days) already re-established a dense, homogenously distributed layer of collagen fibers. Therefore the performance of topographically engineered cellulose patches was superior to the one of identical non-structured patches.

Figure 14:
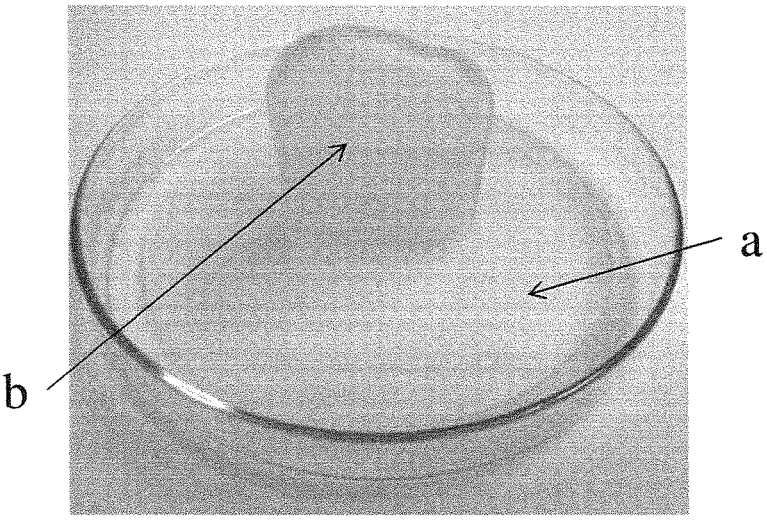
FIG. 14 shows a picture of a 3D PDMS mold with topography.

Making of 3D-Topographically Structured Elements:

3D cellulose structures are obtained by introducing 3D silicone molds with the bacterial culture. The silicone molds feature surface topography, an example is illustrated in FIG. 14. The surface topography is imprinted during the molding process itself (with e.g. PDMS) or applied as additional layer (e.g. by gluing with the PDMS itself an already structured layer, as previously described). The silicone mold has a thickness between 0.5-2 mm and an inner cavity of the shape, sizes and dimensions of the object to be covered with cellulose. The silicone mold can feature an additional layer at its top for facilitating its placement into the bacterial culture.

The silicone mold with surface topography is placed in the bacterial culture so to allow for:
complete wetting of the silicone mold external surface
air filling of the internal cavity.

The placement of the silicone mold can be helped with a bioreactor consisting of two chambers, for air and bacteria in medium, respectively. Oxygen circulation within the air chamber can be facilitated by leaving the chamber open or by controlling the oxygen flow in it, by using e.g. a pump or a gas bottle with a system of valves.

Figure 15:
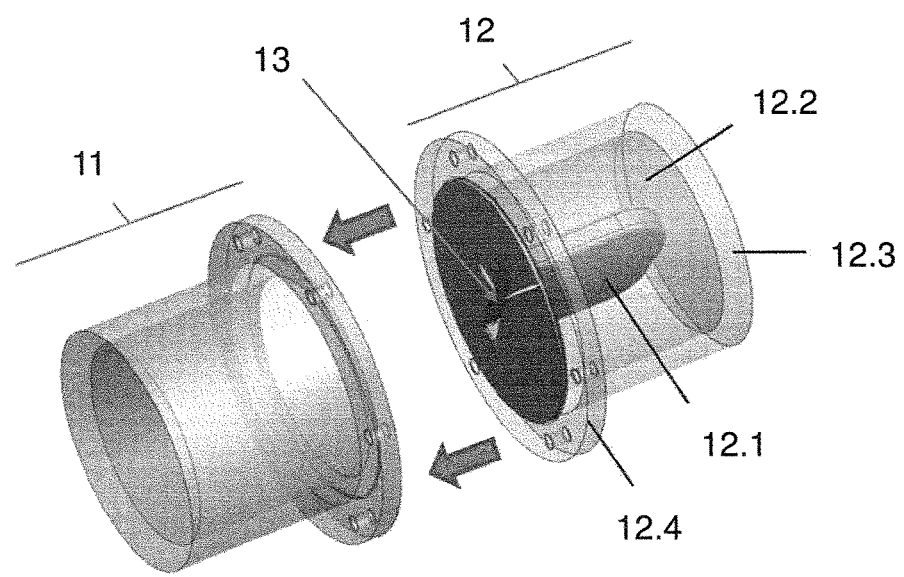
FIG. 15 shows a schematic representation of a bioreactor configuration for the generation of 3D moulds.

A schematic representation of a bioreactor configuration is illustrated in FIG. 15.

After the culturing time, a cellulose layer is formed at the mold interface. The cellulose pouch/cover/pocket features surface topography on its internal surface and can easily be removed, washed, processed and sterilized as previously described for the flat cellulose patches. The cellulose pocket is eventually flipped inside-out in order to feature surface topography on its external surface. The target object can eventually be inserted within the cellulose pocket. The enclosing of the object can be optimized by suturing the open side of the cellulose pocket.

Figure 16:
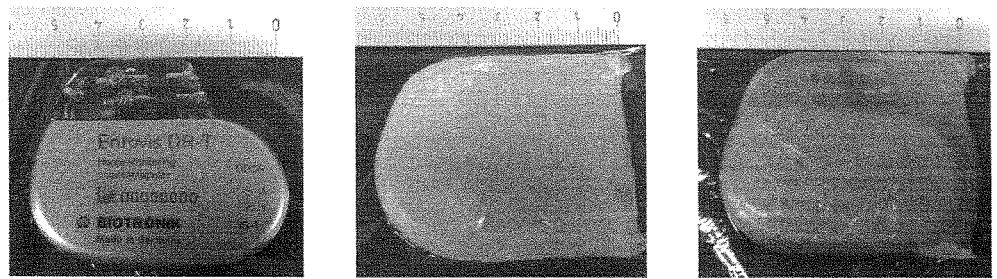
FIG. 16 shows a 3D cellulose pouch/cover/pocket on a pacemaker, left: pacemaker alone, middle: pouch alone; right: pacemaker in pouch.

FIG. 16 illustrates as an example a 3D cellulose pouch/cover/pocket on a pacemaker.

LIST OF REFERENCE SIGNS

| | |
|---|---|
| 1 | COC mask |
| 2 | patterned active surface element, PDMS mold |
| 3 | backside of 2 |
| 4 | frontside of 2, topographic surface |
| 5 | ridge |
| 6 | groove |
| 7 | central mirror plane of the ridge |
| 8 | central mirror plane of the groove |
| 9 | running direction of the pattern |
| 10 | cellulose element |
| 11 | oxygen chamber |
| 12 | fermentation chamber |
| 12.1 | mould |
| 12.2 | tube |
| 12.3 | lid |
| 12.4 | flange |
| 13 | inner cavity for oxygen permeation |
| e | ridge width |
| f | groove width |
| α | pattern angle |
| p | pattern period |
| h | pattern height |
| l | pattern length along running direction of grooves/ridges |

The invention claimed is:

1. A method for the self-assembled production of a topographically surface structured cellulose element comprising:
in a first step, providing a mold, which has on one side a first surface which is, with respect to the topographically surface structured cellulose element to be produced, in a complementary manner topographically surface structured in the form of a regular array of geometric features in at least one direction of the surface plane, and which is permeable to oxygen,
wherein a liquid growth medium containing cellulose producing bacteria is provided, and
wherein the mold is placed to form a liquid/air interface of the liquid growth medium such that the side of the mold with the first surface is in direct contact with the liquid growth medium, and with an opposite side is facing air or a specifically provided oxygen containing gas surrounding, allowing for said bacteria to produce and deposit cellulose on said first surface and developing on the interface therewith a topographically surface structured surface complementary to said first surface, until a contiguous cellulose layer with a thickness of the element of at least 0.3 mm is formed; and
in a second step, removing said element from said mold.

2. The method according to claim 1, wherein the element has a thickness in the range of 0.5-10 mm.

3. The method according to claim 1, wherein the mold has a diffusivity to O2 of at least $10^{-6}$ cm2/s.

4. The method according to claim 1, wherein the mold is made of an oxygen permeable material.

5. The method according to claim 1, wherein the first surface has a topographical structure in the form of a two-dimensional array of pillars, indentations, in the form of an array of ridges/grooves or in the form of a two-dimensional crossing structure or honeycomb patterned structure.

6. The method according to claim 1, wherein the first surface has a topographical structure in the form of a two-dimensional array of pillars or corresponding indentations, wherein the pillars all and regularly have a round, or polygonal, cross-section.

7. The method according to claim 6, wherein the two-dimensional array of pillars or of the corresponding indentations has a periodicity at least in one dimension, or in three different directions, in the range of 5-50 μm, preferably in the range of 7-15 μm.

8. The method according to claim 1, wherein the pillars have a lateral extension in the range of 2-20 μm, and/or wherein the pillars have a height in the range of 0.2-5 μm.

9. The method according to claim 5, wherein the ridges have a height (h) of at least 0.4 μm.

10. The method according to claim 1, wherein in the second step the mold with the element on its topographically surface structured first surface is immersed into a liquid, and the element is removed, from said first surface in said liquid.

11. The method according to claim 1, wherein after the second step the element is heat-treated, for a time span of more than 10 minutes.

12. The method according to claim 1, wherein the mold is made of an oxygen permeable polymeric material, produced in that a topographically complementary structured mask element is used as a template for a liquid applied or injected substrate material, in a soft lithography process, optionally followed by a cross-linking and/or polymerization step, further optionally followed by a surface treatment step, including a plasma treatment step on the topographical surface.

13. The method according to claim 1, wherein the mold is made of an oxygen permeable polymeric PDMS material.

14. The method according to claim 1, wherein the mold is made of an oxygen permeable polymeric PDMS material, produced in that a topographically complementary structured mask element is used as a template for a liquid applied or injected substrate material, in a soft lithography process, optionally followed by a cross-linking and/or polymerization step, further optionally followed by a surface treatment step, including a plasma treatment step on the topographical surface.

15. The method according to claim 1, wherein the first surface has a topographical structure in the form of a two-dimensional array of pillars, indentations, in the form of an array of ridges/grooves or in the form of a two-dimensional crossing structure or honeycomb patterned structure, wherein the width of the positive structures, including of the ridges and/or of the negative structures, and/or of the grooves, is in the range of 0.5-100 μm.

16. The method according to claim 1, wherein the first surface has a topographical structure in the form of a two-dimensional array of pillars, indentations, in the form of an array of ridges/grooves or in the form of a two-dimensional crossing structure or honeycomb patterned structure, wherein the width of the ridges is in the range of 0.5-5 µm and the width of the grooves is in the range of 0.5-5 µm, or both widths being essentially equal.

17. The method according to claim 1, wherein the first surface has a topographical structure in the form of a two-dimensional array of pillars or corresponding indentations, wherein the pillars all and regularly have a circular or oval, or triangular, square, pentagonal or hexagonal cross-section.

18. The method according to claim 6, wherein the two-dimensional array of pillars or of the corresponding indentations has a periodicity at least in one dimension, or in three different directions, in the range of 7-15 µm.

19. The method according to claim 5, wherein the pillars have a lateral extension in the range of 4-10 µm and/or wherein the pillars have a height in the range of 0.5-2 µm.

20. The method according to claim 5, wherein the ridges have a height (h) in the range of 0.5-5 µm or in the range of 0.5-2 µm, or in the range of 1-2 µm.

21. The method according to claim 1, wherein in the second step the mold with the element on its topographically surface structured first surface is immersed into a liquid, and the element is peeled off, from said first surface in said liquid, wherein said liquid is a NaOH solution, with a concentration in the range of 0.5-2 M, wherein in case of a three-dimensional element, in the form of a pouch or pocket, the element is removed from the mold and turned inside out such that the surface of the element facing inside during production is facing outside for use.

22. The method according to claim 1, wherein after the second step the element is heat-treated, by keeping it at a temperature above 60° C. in a NaOH solution, for a time span of more than 10 minutes, or of more than 60 minutes.

23. A method for the self-assembled production of a topographically surface structured cellulose element comprising:
in a first step, providing a mold, which has on one side a first surface which is, with respect to the topographically surface structured cellulose element to be produced, in a complementary manner topographically surface structured, and which is permeable to oxygen, wherein said first surface has a topographical structure in the form of a two-dimensional array of pillars, indentations in the form of an array of ridges/grooves or in the form of a two-dimensional crossing structure or honeycomb patterned structure,
wherein the width of the positive structures, including of the ridges and/or of the negative structures, and/or of the grooves, is in the range of 0.5-100 µm,
wherein a liquid growth medium containing cellulose producing bacteria is provided, and
wherein the mold is placed to form a liquid/air interface of the liquid growth medium such that the side of the mold with the first surface is in direct contact with the liquid growth medium, and with an opposite side is facing air or a specifically provided oxygen containing gas surrounding, allowing for said bacteria to produce and deposit cellulose on said first surface and developing on the interface therewith a topographically surface structured surface complementary to said first surface, until a contiguous cellulose layer with a thickness of the element of at least 0.3 mm is formed; and
in a second step, removing said element from said mold.

24. The method according to claim 23, wherein the two-dimensional array of pillars or of the corresponding indentations has a periodicity at least in one dimension, or in three different directions, in the range of 7-15 µm.

25. The method according to claim 23, wherein the mold is made of an oxygen permeable polymeric siloxane material.

* * * * *